United States Patent [19]

Hemenway

[11] Patent Number: Plant 5,296

[45] Date of Patent: Oct. 23, 1984

[54] VARIETY OF APRICOT TREET

[76] Inventor: Frederick H. Hemenway, 8895 Winters Rd., Winters, Calif. 95694

[21] Appl. No.: 398,763

[22] Filed: Jul. 15, 1982

[52] U.S. Cl. ..... Plt./39

[58] Field of Search ..... Plt./39

*Primary Examiner*—Robert E. Bagwill

*Attorney, Agent, or Firm*—Mark C. Jacobs

[57] ABSTRACT

An apricot tree which bears early ripening, large, freestone fruit and which has a large spreading tree with dark green leaves having red globose glands and a lack of stipules.

2 Drawing Figures

BACKGROUND OF THE VARIETY

The present invention relates to a new and distinct variety of apricot tree characterized by its bearing of fruit which is of good eating quality and relatively early ripening and more particulary charcterized by the fruit being of uniformly large size, uniform shape and having a smooth skin with little or no fuzz.

The commercial value of a fruit tree is dependent upon several factors, the lack of any one of which can affect the price brought by the fruit. The well known Tilton and Royal (unpatented) varieties of apricot trees bear symmetrical fruit of medium to large size and good quality. However, the apricots borne by these varieties ripen later than those borne by other varieties such as the Poino apricot tree (U.S. Plant Pat. No. 2,192)and frequently encounter depressed prices.

Other commercial varieties that are of early season bearing are Derby and Royal. These are found in the orchards of Northern California.

Ofttimes the fruit of early varieties is of inconsistant size, and is considered inferior for this and other reasons, such as poor storage capability.

There has long been a need for an apricot tree which bears fruit that ripens relatively early and whose fruit is of a uniformly large size. Obviously other aesthetic qualities that appeal to consumers are also desirable.

ORIGIN AND ASEXUAL REPRODUCTION OF THE VARIETY

The new variety of apricot tree was discovered growing as a chance seedling in my orchard located in the town of Winters, Yolo County, Calif. The variety was first reproduced by selected grafting onto Marianna 2624 plum rootstock. The variety was reproduced by me primarily because of the fact that I had been attracted to the large size of the fruit on this chance seedling.

SUMMARY OF THE VARIETY

The instant variety has a trunk and branches that are medium in size to those of the Royal variety. However the leaves are larger and of a darker green color. The leaves are of a uniform size and density. In general the tree itself has an appearance similar to many other apricot trees, including the Tilton and the Royal.

The tree bears fruit ready for harvesting three (3) days before Derby and ten (10) days prior to Royal. Thus the earliest ripening fruits are ready for harvesting about June 1st in normal years.

The fruits themselves ripen with a peachy-orange cast. The fruits also have a smooth skin with little or no fuzz generally associated with apricots. The fruits more closely approximate small peaches in size. However, the pit size is the same as that of the Royal Apricot, thereby giving rise to a significantly larger edible portion.

BRIEF DESCRIPTION OF THE DRAWINGS

My new variety of apricot is illustrated by the accompanying drawings by color photography reproduction.

FIG. 1 is a comparison of the fruit of the instant variety compared in size to a commercial smaller variety, namely Royal, each fruit being cut into halves to expose the flesh with the stone remaining in one such half.

FIG. 2 illustrates are leaves of the instant variety.

DETAILED DESCRIPTION OF THE VARIETY

Reference is made to the pomological details of this new and distinct variety of apricot tree, of which the following have been observed. The comparison is made to 'Royal' which is belived to be a well known shipping apricot. Major color code plate identification. If any, are by reference to the A. Maerz and M. Paul Dictionary of color published by the McGraw-Hill Book Company, Second Edition 1950, unless otherwise stated.

Tree:
- *Size.*—Large.
- *Figure.*—Spreading and open.
- *Productivity.*—Productive.
- *Bearing.*—Regular.

Branches:
- *Size.*—Medium.
- *Color.*—"Amber Brown", plate III of Ridgeway.
- *Surface.*—Smooth.
- *Lenticels.*—Less numerous than Royal but otherwise similar.

Leaves:
- *Size.*—Large, smooth and uniform.
- *Shape.*—Ovate, acutely pointed.
- *Thickness.*—Medium.
- *Color.*—Darker green than Royal. Red pigment of new leaves and shoots more intense than Royal.
- *Margin.*—Crenate and finely serrated.
- *Petiole.*—Medium length and thickness.
- *Glands.*—Number 1-2 on petiole at or below blade. Color and Shape — Red Globose. Stipules — None.

Flower buds:

*Size.*—Medium.

*Length.*—Medium of pointed configuration.

Flowers:

*Blooming period.*—Slightly ahead of Royal.

*Color.*—Large and white.

Fruit: Ranges from June 1 to 5, or three (3) days before Derby and ten (10) days before Royal.

*Size.*—Uniformly large.

*Form.*—Firm.

*Suture.*—Extends from base over entire circumference. Marked depression beyond pistil point.

*Ventral surface.*—Slightly rounded throughout with equal lips.

*Stem cavity.*—Rounded.

*Base.*—Rounded.

*Apex.*—Short, rounded to truncate.

*Pistil point.*—Oblique.

Flesh:

*Color.*—"Deep Chrome", plate III of Ridgeway.

*Surface of pit cavity.*—"Cadmium yellow" plate III of Ridgway.

Stone:

*Type.*—Free.

*Base.*—Straight.

*Apex.*—Rounded.

*Sides.*—Equal.

*Surface.*—Regular.

*Ventral edge.*—Small wing throughout.

*Splitting tendency.*—Slight.

The variety of apricot tree described herein possesses the characteristics illustrated and described from being grown in the Central Valley of California. It is understood that variations of the usual magnitude may occur when the growing conditions are different. The color of the "darker green" leaves as viewed against Royal is found to be Empire Green, Plate XXXII of the R. Ridgway book which was copyrighted by the author in 1912 and entitled "Standards of Color Nomenclature".

I claim:

1. A new and distinct variety of apricot tree substantially as described and illustrated which is characterized by large sized, early ripening, freestone fruit whose stones are not commensurate with the size of the fruit, and wherein the tree of said variety is large and spreading; the leaves of which are large, ovate, acutely pointed and dark green with red globose glands; further characterized by medium pointed buds that produce large white flowers slightly ahead of Royal.

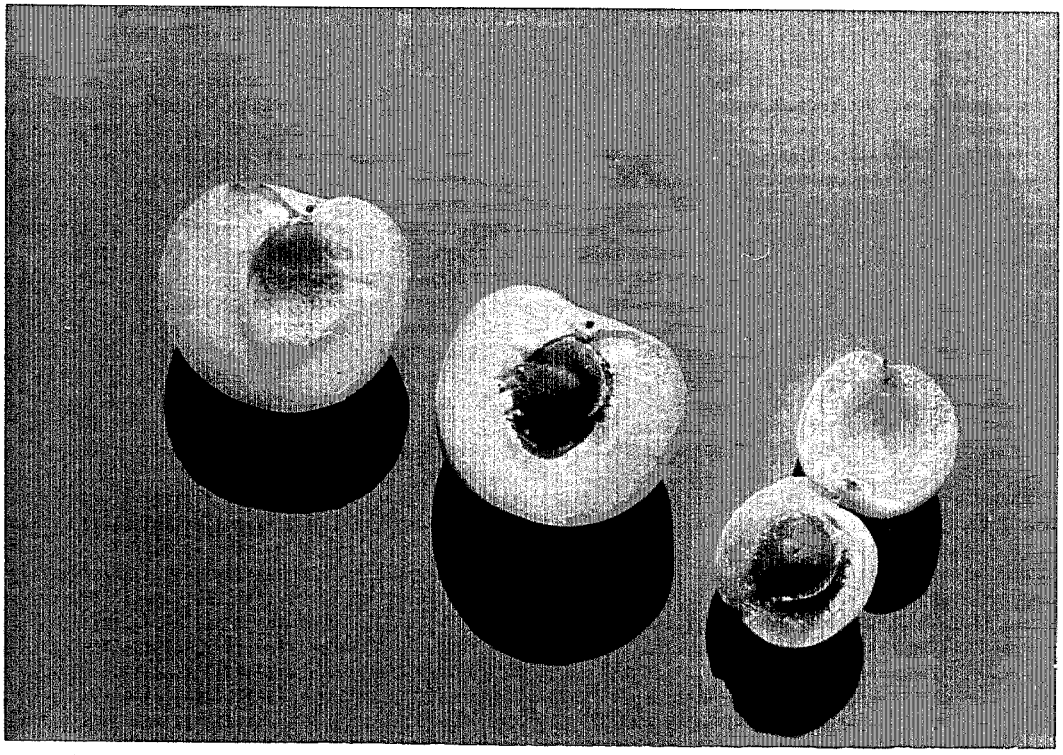
Fig. 1
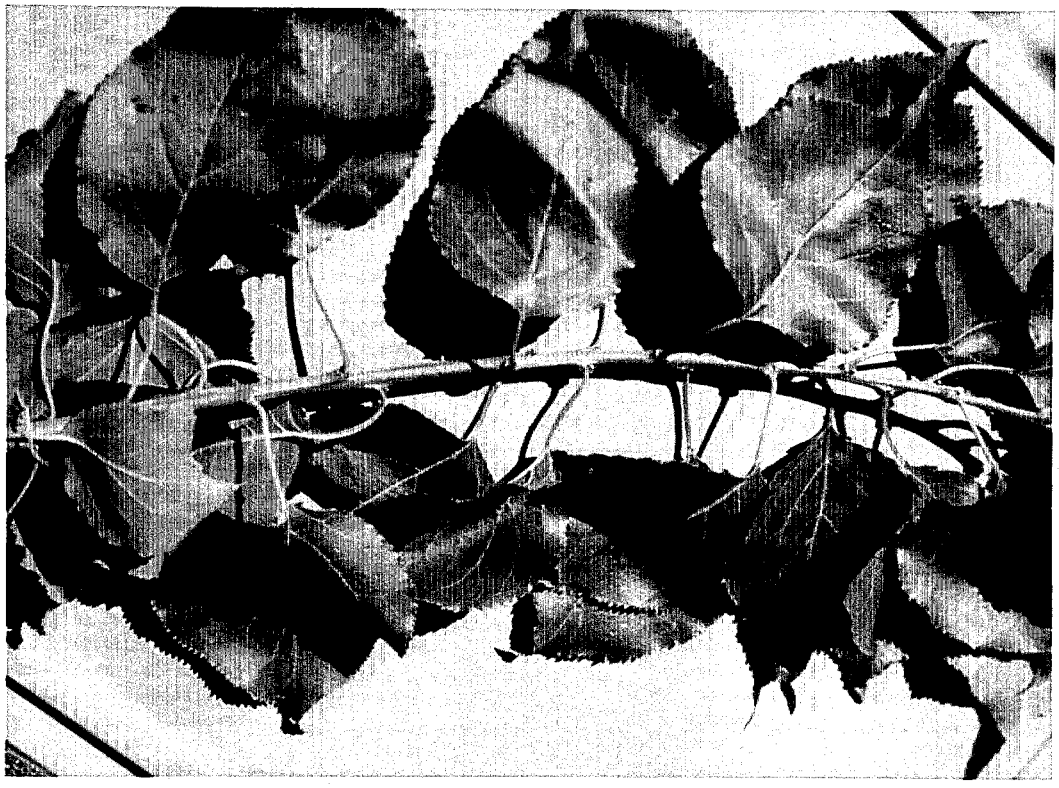

* * * * *